(12) United States Patent
Ayala et al.

(10) Patent No.: US 7,867,521 B2
(45) Date of Patent: *Jan. 11, 2011

(54) ASPARTAME AND CITRATE FLAVORED PHOSPHATE SALT LAXATIVE

(75) Inventors: Nelson Ayala, Lynchburg, VA (US); Michael L. Caswell, Lynchburg, VA (US); Sarah S. Post, Forest, VA (US); Sherrie Scott, Forest, VA (US)

(73) Assignee: C.B. Fleet Company, Incorporated, Lynchburg, VA (US)

( * ) Notice: Subject to any disclaimer, the term of this patent is extended or adjusted under 35 U.S.C. 154(b) by 675 days.

This patent is subject to a terminal disclaimer.

(21) Appl. No.: 11/574,635

(22) PCT Filed: Aug. 9, 2005

(86) PCT No.: PCT/US2005/028132

§ 371 (c)(1),
(2), (4) Date: Sep. 17, 2007

(87) PCT Pub. No.: WO2006/028632

PCT Pub. Date: Mar. 16, 2006

(65) Prior Publication Data

US 2008/0145445 A1    Jun. 19, 2008

Related U.S. Application Data

(63) Continuation of application No. 10/934,638, filed on Sep. 3, 2004, now abandoned.

(51) Int. Cl.
A61K 33/34 (2006.01)
A01N 59/26 (2006.01)

(52) U.S. Cl. ..................... 424/606; 424/601
(58) Field of Classification Search .................. None
See application file for complete search history.

(56) References Cited

U.S. PATENT DOCUMENTS

| | | |
|---|---|---|
| H859 H | 12/1990 | Augustine |
| 5,013,716 A | 5/1991 | Cherukuri et al. |
| 5,106,632 A | 4/1992 | Wong et al. |
| 5,124,144 A | 6/1992 | Giorgetti et al. |
| 5,274,001 A | 12/1993 | Borody |
| 5,498,425 A | 3/1996 | Wood et al. |
| 5,616,346 A | 4/1997 | Aronchick |
| 5,688,529 A | 11/1997 | Lidgate et al. |
| 5,997,906 A | 12/1999 | Wood et al. |
| 6,103,268 A | 8/2000 | Borody et al. |
| 6,156,332 A | 12/2000 | Bakal et al. |
| 6,162,464 A | 12/2000 | Jacob et al. |
| 6,361,799 B1 | 3/2002 | Palkhiwala |
| 6,737,068 B2 | 5/2004 | Durden |
| 6,806,256 B2 | 10/2004 | Ulrich et al. |
| 6,866,873 B2 | 3/2005 | Stern |
| 6,906,038 B2 | 6/2005 | Mazer |
| 6,946,149 B2 | 9/2005 | Cleveland |
| 7,101,572 B2 | 9/2006 | Santos et al. |
| 7,169,381 B2 | 1/2007 | Barras et al. |
| 7,332,184 B2 | 2/2008 | Vanner et al. |
| 2002/0137803 A1 | 9/2002 | Kirkland |
| 2004/0071779 A1 | 4/2004 | Keiser et al. |
| 2004/0101491 A1 | 5/2004 | Stier |
| 2004/0115282 A1 | 6/2004 | Keiser et al. |
| 2004/0143005 A1 | 7/2004 | Barras et al. |
| 2004/0170698 A1 | 9/2004 | Halow |
| 2004/0192614 A1 | 9/2004 | Vanner et al. |
| 2005/0061861 A1 | 3/2005 | Pennino |
| 2005/0271749 A1 | 12/2005 | Borody et al. |
| 2006/0051428 A1 | 3/2006 | Ayala et al. |
| 2007/0082061 A1 | 4/2007 | Ayala et al. |
| 2007/0207216 A1 | 9/2007 | Caswell |
| 2008/0044489 A1 | 2/2008 | Caswell |
| 2008/0145445 A1 | 6/2008 | Ayala et al. |

FOREIGN PATENT DOCUMENTS

| | | |
|---|---|---|
| BE | 541665 | 8/1959 |
| EP | 0396165 | 11/1990 |
| WO | WO89/05659 | 6/1989 |
| WO | WO 93/17589 | 9/1993 |
| WO | WO 94/12191 | 6/1994 |
| WO | WO 98/43654 | 10/1998 |
| WO | WO 2004/032926 | 4/2004 |
| WO | WO 2004/037292 | 5/2004 |
| WO | WO 2006/028632 | 3/2006 |
| WO | WO 2006/118562 | 11/2006 |
| WO | WO 2007/044681 | 4/2007 |

OTHER PUBLICATIONS

Rao, "Toxicologic Pathology of the Kidney and Urinary Bladder," Toxicologic Pathology, vol. 30, No. 6, pp. 651-656, 2002.

Vanner et al., "A Randomized Prospective Trial Comparing Oral Sodium Phosphate with Standard Polyethylene Glycol-Based Lavage Solution (Golytely) in the Preparation of Patients for Colonoscopy," The American Journal of Gastroenterology, vol. 85, No. 4, pp. 422-427, 1990.

(Continued)

Primary Examiner—Ernst V Arnold
(74) Attorney, Agent, or Firm—Evan Law Group LLC

(57) ABSTRACT

The present invention provides compositions, kits, and methods suitable for cleansing the colon before colonoscopy. The compositions include a phosphate salt and a flavorant that includes aspartame and a citrate. The kits include the previously mentioned compositions and also may include suitable containers, packaging, relief wipes, and instructions for use. The methods may include administering orally to a subject an aqueous preparation including monobasic sodium phosphate, dibasic sodium phosphate, aspartame, and citric acid.

11 Claims, 2 Drawing Sheets

OTHER PUBLICATIONS

Toblli et al., "Potassium citrate administration ameliorates tubulointerstitial lesions in rats with uric acid nephropathy," Clinical Nephrology, vol. 55, No. 1, pp. 59-68, 2001.

Lacour et al., "Ellet du citrate et des phosphate sur le transport du calcium dans l'iléon de rat in vitro," Gastroenterol Clin. Biol., 18, pp. 938-944, 1994. (Summary in English).

Oikawa et al., "Modulation of plasminogen activator inhibitor-1 in vivo : A new mechanism for the anti-fibrotic effect of rennin-angiotensin inhibition," Kidney International, vol. 51, pp. 164-172, 1997.

Marangella et al., "Crystallization Inhibitors in the Pathophysiology and Treatment of Nephrolithiasis," Urologia Int., 72, Suppl. 1, pp. 6-10, 2004.

Neuhofer et al., "Chronic COX-2 inhibition reduces medullary HSP70 expression and induces papillary apoptosis in dehydrated rats," Kidney International, vol. 65, pp. 431-441, 2004.

Ma et al., "Model of robust induction of glomerulosclerosis in mice: Importance of genetic background," Kidney International, vol. 64, pp. 350-355, 2003.

Smoyer et al., "Ischemic Acute Renal Failure Induces Differential Expression of Small Heat Shock Proteins," J Am Soc Nephrol, 11, pp. 211-221, 2000.

Desmeules et al., "Acute Phosphate Nephropathy and Renal Failure," NEJM, 349, pp. 1006-1007, 2003.

Markowitz et al., "Acute Phosphate Nephropathy following Oral Sodium Phosphate Bowel Purgative: An Underrecognized Cause of Chronic Renal Failure," J Am Soc Nephrol, 16, pp. 3389-3396, 2005.

Markowitz et al., "Renal Failure Due to Acute Nephrocalcinosis Following Oral Sodium Phosphate Bowel Cleansing," Human Pathology, 35, 675-684, 13 pages total, 2004.

Ritskes-Hoitinga et al., "Phosphorus-Induced Nephrocalcinosis and Kidney Function in Female Rats," J. Nutr., 119, pp. 1423-1431, 1989.

Orias et al., "Extreme Hyperphosphatemia and Acute Renal Failure after a Phosphorus-Containing Bowel Regimen," Am J Nephrol, 19, pp. 60-63, (1999).

Fine et al., "Severe Hyperphosphatemia Following Phosphate Administration for Bowel Preparation in Patients With Renal Failure: Two Cases and a Review of the Literature," American Journal of Kidney Diseases, vol. 29, No. 1, pp. 103-105, (1997).

Wangoo et al., "Chronobiology of urinary citrate excretion amongst stone-fomers and healthy males from North Western India", Urological Research, 19:203-206, (1991).

Moeckel et al, "Distribution of de novo synthesized betaine in rat kidney: role of renal synthesis on medullary betaine accumulation," Am. J. Physiol., 272, pp. F94-F99, (1997).

Moeckel et al, "COX2 Activity Promotes Organic Osmolyte Accumulation and Adaptation of Renal Medullary Interstitial Cells to Hypertonic Stress," Journal of Biological Chemistry, vol. 278, No. 21, pp. 19352-19357, (2003).

Moeckel et al., "Role of integrin $\alpha_1\beta_1$ in the regulation of renal medullary osmolyte concentration," Am J Physiol Renal Physiol, 290, pp. F223-F231, (2006).

Marshall et al., "Prospective, randomized trial comparing sodium phosphate solution with polyethylene glycol-electrolyte lavage for colonoscopy preparation," Gastrointestinal Endoscopy, vol. 39, No. 5, pp. 631-634, (1993).

Petsite.com Ltd., "Amazing Rodent Facts," located at http://www.petalia.com.au/templates/StoryTemplate_Process.cfm?Story_No=350, p. 1, printed Nov. 2007.

Nie et al., "Distinct Contributions of T1R2 and T1R3 Taste Receptor Subunits to the Detection of Sweet Stimuli," Current Biology, vol. 15, pp. 1948-1952, (2005).

International Food Information Council Foundation, "Everything You Need to Know About Sucralose," 2 pages, (1998).

International Food Information Council Foundation, "Everything You Need to Know About Acesulfame Potassium," 2 pages, (1998).

Calorie Control Council, "Low-Calorie Sweeteners: Acesulfame Potassium," can be found at http://www.caloriecontrol.org/acesluf.html, 3 pages, (2004).

International Food Information Council Foundation, "Low-Calorie Sweeteners:Adding Reduced-Calorie Delights to a Healthful Diet," can be found at http://www.ific.org/foodinsight/1998/jf/lcsfi198.cfm?renderforprint=1, 4 pages, (1998).

International Food Information Council Foundation, "More Choices For The Sweet Life," can be found at http://www.ific.org/foodinsight/2002/so/morechoicesfi502.cfm?renderforprint=1, 3 pages, (2002).

FoodProductionDaily.com/Europe, "Sweet taste study promises perfect sugar replacement," can be found at http://www.foodproductiondaily.com/news/printNewsBis.asp?id=63743, 2 pages, (2005).

International Search Report dated Mar. 29, 2007 for application No. PCT/US2006/039419.

Khashab, M. et al., "Efficacy and tolerability of a new formulation of sodium phosphate tablets (INKP-101), and a reduced sodium phosphate dose, in colon cleansing: a single-center open-label pilot trial", Aliment Pharmacol Ther., vol. 21, pp. 465-468, (2005).

Rex, D.K. et al., "Safety and efficacy of two reduced dosing regimens of sodium phosphate tablets for preparation prior to colonoscopy", Aliment Pharmacol Ther., vol. 16, pp. 937-944, (2002).

Salix Pharmaceuticals, Inc., "Visicol® Product Information", http://www.salix.com/products_visicol.aspx, 1 page, printed on Aug. 16, 2006.

InKine Pharmaceutical Company, Inc., "INIKP-102 Tablet Posters; A new purgative from InKine Pharmaceutical Company, Inc., a subsidiary of Salix Pharmaceuticals", American College of Gastroenterology, Annual Scientific Meeting, 28 pages, Oct. 30-Nov. 2, 2005.

Gatorade Sports Science Institute, "Roundtable; Intestinal fluid absorption in exercise and disease", SSE Roundtable #11, found at http://gssiweb.com/Article_Detail.aspx?articleid=50&level=4&topic=5, vol. 4, No. 1, 5 pages, (1993), (2002).

McNaught, A.D. "Nomenclature of carbohydrates; recommendations 1996", Pure & Applied Chemistry, vol. 68, No. 10, pp. 1919-2008, (1996).

Gatorade Beverage Comparison Chart, http://www.gssiweb.com/pdf/gatorade_bev_chart.pdf#search=%22gatorade%20beverage%20comparison%20chart%22, 2 pages, printed Sep. 2005.

Sports Drink Comparisons, The University of Arizona, Group 14, Honors Biology 181, Fall 1998, found at http://student.biology.arizona.edu/honors98/group14/sportsdrinks.html, 2 pages, printed on Feb. 25, 2008.

Accelerade, "Sports Drink Comparison", PacificHealth Laboratories, Inc., found at http://www.accelerade.com/pages/product_compare.html, 1 page, printed on Sep. 29, 2005.

All-Sport Body Quencher, "Product Comparison", found at http://www.drinkallsport.com/pop/product_compare.htm, 1 page, printed on Sep. 29, 2005.

Afridi, S.A. et al., "Prospective, randomized trial comparing a new sodium phosphate-bisacodyl regimen with conventional PEG-ES lavage for outpatient colonoscopy preparation," Gastrointestinal Endoscopy, pp. 485-489, vol. 41, (1995).

Arezzo, A. "Prospective randomized trial comparing bowel cleaning preparations for colonoscopy," Surgical Laparoscopy: Endoscopy & Percutaneous Techniques, pp. 215-217, vol. 10, No. 4, (2000).

Aronchick, C.A. et al., "A novel tableted purgative for colonoscopic preparation: efficacy and safety comparisons with Colyte and Fleet Phospho-Soda," Gastrointestinal Endoscopy, pp. 346-352, vol. 52, No. 3, (2000).

Avery, M.E. et al., "Oral therapy for acute diarrhea: The underused simple solution," The New England Journal of Medicine, pp. 891-894, vol. 323, No. 13, (1990).

Barclay, R.L. et al., "Carbohydrate-electrolyte rehydration protects against intravascular volume contraction during colonic cleansing with orally administered sodium phosphate", Gastrointestinal Endoscopy, pp. 633-638, vol. 56, No. 5, (2002).

Bawani, M. et al., "A Single Blinded, Prospectively Randomized Comparison of Oral Phosphosoda (OP) with Polyethylene Glycol Based Solution (PG) as a Colonic Lavage for Colonoscopy," Am. J. Gastroent., p. 1350, vol. 86, Abstract 239, (1991).

Bawani, M.H. et al., "A Single Blind Control Study of Fleet Oral Phosphosoda Laxative and Magnesium Citrate for Colonoscopy Preparation," AJG, p. 1964, vol. 91, Abstract 316, (1996).

Berkelhammer, C. et al., "Low-Volume Oral Colonoscopy Bowel Preparation: Sodium Phosphate and Magnesium Citrate," Gastrointestinal Endoscopy, pp. 89-94, vol. 56, No. 1, (2002).

Bujnada, L. et al., "Tolerance and Colon Cleansing with Two Preparations. Polyethylene Glycol Versus Sodium Phosphate," Gastroenterologia Y. Hepatologia, pp. 9-12, vol. 24, (2001).

Chaleoykitti, B., "Comparative Study Between Polyethylene Glycol and Sodium Phosphate Solution in Elective Colorectal Surgery," J. Med. Assoc. Thai, pp. 92-96, vol. 85, (2002).

Chan, A. et al., "Use of Oral Sodium Phosphate Colonic Lavage Solution by Canadian Colonoscopists: Pitfalls and Complications," Can J. Gastroenterol., pp. 334-338, vol. 11, No. 4, (1997).

Chia, Y.W. et al., "Role of Oral Sodium Phosphate and Its Effectiveness in Large Bowel Preparation for Out-Patient Colonoscopy," J.R. Coll. Surg. Edinb., pp. 374-376, vol. 40, (1995).

Chilton, A.P. et al., "A Blinded, Randomized Comparison of a Novel, Low-Dose, Triple Regimen with Fleet Phospho-Soda: A Study of Colon Cleanliness, Speed and Success of Colonoscopy," Endoscopy, pp. 37-41, vol. 32, No. 1, (2000).

Clarkston, W.K. et al., "Oral sodium phosphate versus sulfate-free polyethylene glycol electrolyte lavage solution in outpatient preparation for colonoscopy: a prospective comparison," Gastrointest. Endosc., pp. 42-48, vol. 43, (1996).

Cohen, S.M. et al., "Prospective, randomized, endoscopic-blinded trial comparing precolonoscopy bowel cleansing methods," Dis. Colon Rectum, pp. 689-696, vol. 37, (1994).

Da Silva, M.M. et al., "Colonoscopy preparation in children: safety, efficacy, and tolerance of high- versus low-volume cleansing methods," Journal of Pediatric Gastroenterology and Nutrition, pp. 33-37, vol. 24, (1997).

Del Piano, M. et al., "A comparison of 3 methods of preparation for colonoscopy," Minerva Gastroenterol. Dietol, pp. 89-92, vol. 39, (1993).

Fernandez, J.M.P. et al., "Characterization of the safety, effectiveness and use of oral sodium phosphate," Revista Espanola De Enferm. Digestivas, pp. 220-225, vol. 93, No. 4, (2001).

Frommer, D. "Cleansing ability and tolerance of three bowel preparation for colonoscopy," Dis. Colon Rectum, pp. 100-104, vol. 40, (1997).

Golub, R.W. et al., "Colonoscopic Bowel Preparations—Which One?," Dis. Colon. Rectum., pp. 594-599, vol. 38, (1995).

Greenleaf, J.E. et al., "Plasma volume expansion with oral fluids in hypohydrated men at rest and during exercise," Aviat Space Environ. Med., pp. 837-844, vol. 69, (1998).

Gremse, D.A. et al., "Comparison of oral sodium phosphate to polyethylene glycol-based solution for bowel preparation for colonoscopy in children," J. Ped. Gast. And Nutrition, pp. 586-590, vol. 23, (1996).

Habr-Gama, A., "Bowel preparation for colonoscopy: comparison of mannitol and sodium phosphate: results of a prospective randomized study," Rev. Hosp. Clin. Fac. Med. S. Paulo, pp. 187-192, vol. 54, No. 6, (1999).

Handelsman, J.C. et al., "Experience with ambulatory preoperative bowel preparation at the Johns Hopkins hospital," Arch. Surg., pp. 441-444, vol. 128, (1993).

Haroon, et al., "A randomized clinical trial comparing oral sodium phosphate (NaP) with standard polyethylene glycol-based lavage solution (Colyte) in the preparation of patients for colonoscopy," Gastroenterology, vol. 102, No. 4, Abstract No. 2112, (1992).

Henderson, J.M. et al., "Single-day, divided-dose oral sodium phosphate laxative versus intestinal lavage as preparation for colonoscopy: efficacy and patient tolerance," Gastrointest. Endoscopy, pp. 238-243, vol. 42, No. 3, (1995).

Hookey, L.C. et al., "The safety profile of oral sodium phosphate for colonic cleansing before colonoscopy in adults", Gastrointest. Endoscopy, vol. 56, No. 6, pp. 895-902, (2002).

Huynh, T. et al., "Safety profile of 5-h oral sodium phosphate regimen for colonoscopy cleansing: lack of clinically significant hypocalcemia or hypovolemia," Am. J. Gastroenterol., pp. 104-107, vol. 90, (1995).

Johnson, D.R. et al., "Dehydration and orthostatic vital signs in women with hyperemesis gravidarum" Acad. Emerg. Med., pp. 692-697, (7 pages including correction), vol. 2, (1995).

Kim, M. et al., "Patient compliance and satisfaction with oral bowel preparation for outpatient colonoscopy: a prospective, randomized, blinded trial," Dis. Colon Rectum, vol. 40, pp. A42, Abstract No. P48, (1997).

Klein, S. et al., "Enteral and parenteral nutrition," Sleisenger and Fordtran's Gastrointestinal and Liver Disease, pp. 254-277, (1998).

Kolts, B.E. et al., "A comparison of the effectiveness and patient tolerance of oral sodium phosphate, castor oil, and standard electrolyte lavage for colonoscopy or sigmoidoscopy preparation," Am. J. Gastroenterol., pp. 1218-1223, vol. 88, No. 8, (1993).

Kuchel, G.A. et al., "Cardiovascular responses to phlebotomy and sitting in middle-aged and elderly subjects," Arch. Int. Med., pp. 366-370, vol. 152, (1992).

Lapalus, M-G. et al., "Prospective randomized single-blind trial comparing oral sodium phosphate and polyethylene glycol based solution for colonoscopy preparation," Gastroenterol. Clin. Biol., pp. 29-34, vol. 25, (2001).

Lee, J. et al., "A prospective randomised study comparing polyethylene glycol and sodium phosphate bowel cleansing solutions for colonoscopy," The Ulster Medical Journal, pp. 68-72, vol. 68, No. 2, (1999).

McGee, S.R., "Physical examination of venous pressure: a critical review," Am. Heart J., pp. 10-18, vol. 136, (1998).

Macari, M. et al., "Effect of different bowel preparations on residual fluid at CT colonography," Radiology, pp. 274-277, vol. 218, (2001).

Macleod, A.J.M. et al., "A comparison of fleet phospho-soda with picolax in the preparation of the colon for double contrast barium enema," Clinical Radiology, pp. 612-614, vol. 53, (1998).

Marshall, J.B. et al., "Short report: prospective, randomized trial comparing a single dose sodium phosphate regimen with PEG-electrolyte lavage for colonoscopy preparation," Aliment Pharmacol. Ther., pp. 679-682, vol. 7, (1993).

Marshall, J.B. et al., "Prospective, randomized trial comparing sodium phosphate solution with polyethylene glycol-electrolyte lavage for colonoscopy preparation," Gastrointest. Endosc., pp. 631-634, vol. 39, No. 5, (1993).

Martinek, J. et al., "Cisapride does not improve precolonoscopy bowel preparation with either sodium phosphate or polyethylene glycol electrolyte lavage," Gastrointest. Endoscopy, pp. 180-185, vol. 54, No. 2, (2001).

Maughan, R.J. et al., "Post-exercise rehydration in man: effects of electrolyte addition to ingested fluids," Eur. J. Appl. Physiol. Occup. Physiol., pp. 209-215, vol. 69, (1994).

O'Donovan, A.N. et al., "A prospective blinded randomized trial comparing oral sodium phosphate and polyethylene glycol solutions for bowel preparation prior to barium enema," Clin. Radiology, pp. 791-793, vol. 52, (1997).

Oliveria, L.C.C. et al., "Mechanical bowel preparation for elective colorectal surgery; a prospective, randomized, surgeon-blinded trial comparing sodium phosphate and polyethylene glycol-based oral lavage solutions," Dis. Colon Rectum, pp. 585-591, vol. 40, (1997).

Poon, C.M. et al., "Two liters of polyethylene glycol-electrolyte lavage solution versus sodium phosphate as bowel cleansing regimen for colonoscopy: a prospective randomized controlled trial," Endoscopy, pp. 560-563, vol. 34, (2002).

Rex, D.K. et al., "Impact of bowel preparation on efficacy and cost of colonoscopy," Am. J. Gastroenterology, pp. 1696-1700, vol. 97, No. 7, (2002).

Shaoul, R. et al., "Symptoms of hyperphosphatemia, hypocalcemia, and hypomagnesemia in an adolescent after the oral administration of sodium phosphate in preparation for a colonoscopy," Gastrointest. Endosc., pp. 650-652, vol. 53, No. 6, (2001).

Sudduth, R.H. et al., "The effectiveness of simethicone in improving visibility during colonoscopy when given with a sodium phosphate solution: a double-blind randomized study," Gastrointest. Endoscopy, pp. 413-415, vol. 42, No. 5, (1995).

Thomson, A. et al., "Bowel preparation for colonoscopy: a randomized prospective trial comparing sodium phosphate and polyethylene glycol in a predominantly elderly population," J. Gast. and Hepatology, pp. 103-107, vol. 11, (1996).

Unal, S. et al., "A randomized prospective trial comparing 45 and 90-ml oral sodium phosphate with X-Prep in the preparation of patients for colonoscopy," Acta. Gastro-Enterol. Belg., pp. 281-284, vol. 61, (1998).

Wolff, B.G. et al., "A new bowel preparation for elective colon and rectal surgery: a prospective, randomized clinical trial," Arch. Surg., pp. 895-900, vol. 123, (1998).

Yoshioka, K. et al., "Randomized trial of oral sodium phosphate (picolax) for elective colorectal surgery and colonoscopy," Dig. Surg., pp. 66- 70, vol. 17, (2000).

Young, C.J. et al., "Oral sodium phosphate solution is a superior colonoscopy preparation to polyethylene glycol with bisacodyl," Dis. Colon Rectum, pp. 1568-1571, vol. 43, (2000).

Tjandra, J. et al., "Carbohydrate-Electrolyte (E-Lyte®) Solution Enhances Bowel Preparation With Oral Fleet® Phospho-soda®", Dis Colon Rectum, 47, pp. 1181-1186, (2004).

Canard, J. et al., "Fleet® Phospho Soda: for Greater Acceptability of the Colic Preparation Before Colonoscopy. Randomized Comparative Single Blind Study Versus Polyethylene Glycol." Acta. Endoscopica, pp. 703-708, vol. 31, (2001).

Translation of the Canard, J., et al reference.

Oliveira, L. et al., "Mechanical Bowel Preparation With Oral Sodium Phosphate Solution for Colonoscopy. A New Small Volume Solution Compared to the Traditional Mannitol.", Revista do Colegio Brasileiro de Cirurgioes, pp. 353-358, vol. 26, (1999).

Translation of the Oliveira, L. et al reference.

Salix Pharmaceuticals, Inc., Visicol© Tablets Product Information, 2 pages, (2005).

Verghese, V.J., et al., "Low-salt Bowel Cleansing Preparation (LoSo Prep) as Preparation for Colonoscopy: A Pilot Study", Aliment Pharmacol Ther, vol. 16, pp. 1327-1331, (2002).

Reddy, D., et al., "Efficacy and Safety of Oral Sodium Phosphate Versus Polyethylene Glycol Solution for Bowel Preparation for Colonoscopy", Indian Journal of Gastroenterology, vol. 21, pp. 219-221, (2002).

Martinek, J., et al., "Preparation of the Gut Before Colonoscopy", Prakt., vol. 82, pp. 472-476, (2002). (original and translated version).

Web Page: Wild Resolver, Obtained from: www.wild.de/wild/opencms/en/innovation/technology/wild_innovation_technology_resolver.html, p. 1, Dated: Aug. 20, 2004.

Web Page: Crystal Light Product Information, Obtained from: www.kraftfoods.com/crystallight/cl_products.html, pp. 1-2, Feb. 17, 2004.

Web Page: Kraft Food Products, Pink Lemonade, Obtained from: www.kraftfoods.com/knet_print_version.aspx?s=product&m=product/product_display&Product=4300095019&print_show=1&U3=****4300095019*, p. 1, Dated: May 19, 2004.

Web Page: Kraft Food Products, Lemonade, Obtained from: www.kraftfoods.com/knet_print_version.aspx?s=product&m=product/product_display&Product=4300095023&print_show=1&U3=****4300095023*, p. 1, Dated: May 19, 2004.

Web Page: Kraft Food Products, Sunrise Classic Orange, Obtained from: www.kraftfoods.com/knet_print_version.aspx?s=product&m=product/product_display&Product=4300094541&U3=****4300094541*, p. 1, Dated: May 18, 2004.

Web Page: Kraft Food Products,Tangerine Strawberry, Obtained from: www.kraftfoods.com/knet_print_version.aspx?s=product&m=product/product_display&Product=4300095024&U3=****4300095024*, p. 1, Dated: May 19, 2004.

Web Page: Kraft Food Products, Rasberry Ice, Obtained from: www.kraftfoods.com./knet_print_version.aspx?s=product&m=product/product_display&Product=4300095028&print_show=1&U3=****4300095028*, p. 1, Dated: May 19, 2004.

Web Page: Kraft Food Products, Rasberry Peach, Obtained from: www.kraftfoods.com/knet_print_version,aspx?s=product&m=product/product_display&Product=4300095026&print_show=1&U3=****4300095026*, p. 1, Dated: May 19, 2004.

Anonymous, "Product Information—Crystal Light Iced Tea Decaffeinated Sugar Free"., http://www.kraftfoods.com/main.aspx?s=product&m=product/Product_display&Site=1&Product=4300095016, Dec. 2, 2005.

Anonymous, "Product Information—Jell-O Gelatin Dessert Orange 0 carb Sugar Free 10.2g"., hrrp://www.greatlowcarb.com/product.php?p=4085?w=100>., Dec. 2, 2005.

International Search Report dated Jan., 11, 2006 for corresponding PCT application No. PCT/US2005/028132.

Web Page: Crystal Light-Lemonade-Pink Lemonade Sugar Free Product Information, Obtained from: http://www.kraftfoods.com/knet_print_version.aspx?s=product&m=product/product_display&Product=4300095019&print_show=1, 1 page, printed Apr. 30, 2007.

Web Page: Crystal Light-Lemonade-Raspberry Lemonade Sugar Free Product Information, Obtained from: http://www.kraftfoods.com/knet_print_version.aspx?s=product&m=product/product_display&Product=4300094963&print_show=1, 1 page, printed Apr. 30, 2007.

Web Page: Crystal Light-Fruit Drinks-Strawberry-Kiwi Sugar Free Product Information, Obtained from: http://www.kraftfoods.com/knet_print_version.aspx?s=product&m=product/product_display&Product=4300095008&print_show=1, 1 page, printed Apr. 30, 2007.

Web Page: Crystal Light-Fruit Drinks-Strawberry-Orange-Banana Sugar Free Product Information, Obtained from: http://www.kraftfoods.com/knet_print_version.aspx?s=product&m=product/product_display&Product=4300095009&print_show=1, 1 page, printed Apr. 30, 2007.

Web Page: Crystal Light-Fruit Drinks-Pineapple-Orange Sugar Free Product Information, Obtained from: http://www.kraftfoods.com/knet_print_version.aspx?s=product&m=product/product_display&Product=4300095022&print_show=1, 1 page, printed Apr. 30, 2007.

Web Page: Crystal Light-Sunrise-Sunrise Ruby Red Grapefruit Product Information, Obtained from: http://www.kraftfoods.com/knet_print_version.aspx?s=product&m=product/product_display&Product=4300097199&print_show=1, 1 page, printed Apr. 30, 2007.

Anal itching (online) retrieved from the internet [http://www.cnn.com/HEALTH/library/DS/00453.html]; pp. 1-4, May 5, 2006, [retrieved on Nov. 5, 2006].

Met-Rx Berry Drink Data sheet online http://www.physicallyelite.com/store/store.cfm?do=detail&product_id=12384, pp. 1-5, [retrieved Mar. 21, 2002].

Myoplex datasheet online http://eas.com/index.asp, Myoplex pp. 1-2, [retrieved Nov. 10, 2000].

Ingredient list for EAS Myoplex original nutrition shake, 2 pages, 2001.

Isbrucker, R.A. et al., "Risk and safety assessment on the consumption of licorice root (*Glycyrrhiza* sp.), its extract and powder as a food ingredient, with emphasis on the pharmacology and toxicology of glycyrrhizin", Regulatory Toxicology and Pharmacology, vol. 46, pp. 167-192, (2006).

Translation of the Belgium Patent BE 541665 dated Aug. 1959.

ASPARTAME AND CITRATE FLAVORED PHOSPHATE SALT LAXATIVE

REFERENCE TO RELATED APPLICATIONS

The present application is a continuation application of U.S. application Ser. No. 10/934,638 entitled "Aspartame And Citrate Flavored Phosphate Salt Laxative" filed Sep. 3, 2004 now abandoned.

BACKGROUND

Colonoscopy screening coupled with polyp removal (polypectomy) significantly reduces the incidence of colorectal carcinoma. Unfortunately, of the 147,500 new cases of colorectal carcinoma diagnosed in 2003, the American Cancer Society estimates that only 37% of these cases were diagnosed early enough for treatment to offer the best possible prognosis.

Colonoscopy screening should be repeated more frequently for subjects who have previously undergone a polypectomy due to their increased risk of recurrent polyp formation. However, in a follow-up phase of the National Polyp Study, at least 20% of subjects who had previously undergone polypectomies failed to return for their follow-up screening. In a more recent study, where 8,865 subjects who had previously undergone a polypectomy underwent a second colonoscopy screening, 2,704 (30.5%) were diagnosed with recurrent polyps. A statistical analysis based on the data from this report projected that 50% of subjects will have recurrent polyps within 7.6 years. Despite this level of risk, many subjects do not undergo additional screening.

Prior to colonoscopy, including virtual colonoscopy procedures, the colon must be cleansed so the surgeon may see any polyps that exist on the interior wall of the colon. Furthermore, the colon also must be cleansed before radiological or surgical procedures involving the colon. This cleansing generally entails the drinking of one or more laxative solutions. Aqueous solutions of sodium phosphate salts (monobasic and dibasic sodium phosphate), such as FLEET® PHOSPHO-SODA®, are very effective oral laxatives and are extensively used prior to colonoscopy, radiographic procedures, and surgery. For pre-colonoscopy use, a split regimen is often preferred that includes one 45 mL dose given the evening before colonoscopy and a second 45 mL dose given at least three hours prior to the procedure on the following morning.

One of the main reasons subjects cite for avoiding colonoscopy re-screening is the unpleasant taste of these phosphate based laxative solutions. Depending on the study, from 15 to 51% of the subjects report discomfort in the form of nausea and vomiting. The extremely salty taste of the laxative solution is believed to be the cause of this discomfort. Frequently, subjects cannot tolerate the ingestion of the complete initial dose of the preparation, which often prevents them from consuming more than a small portion of the second dose.

Thus, there is an ongoing need for better tasting laxative solutions suitable for pre-colonoscopy colon cleansing. A better tasting pre-colonoscopy laxative could increase subject compliance with re-screening appointments. This increased compliance regarding consumption of the laxative solution could reduce the need for repeat procedures attributable to inadequate colon cleansing. The materials and methods of the present invention provide phosphate salt laxatives that are significantly more palatable than conventional phosphate salt laxatives.

SUMMARY

Colonoscopy screening coupled with polyp removal significantly reduces the incidence of colon cancer. Prior to colonoscopy, the colon must be cleansed so the surgeon may see any polyps that exist on the interior wall of the colon. Aqueous solutions of sodium phosphate salts, such as FLEET® PHOSPHO-SODA®, are very effective oral laxatives and are extensively used prior to colonoscopy. One of the main reasons subjects cite for avoiding colonoscopy re-screening is the unpleasant taste of these phosphate salt based laxative solutions.

The present invention makes use of the discovery that adding a flavorant that includes aspartame and a citrate, such as citric acid and citrate salts, such as sodium and potassium citrate, to a phosphate salt laxative significantly increases the palatability of the laxative. The resultant flavorant/phosphate salt formulations may increase the subject's willingness to consume the laxative, thus decreasing the repeat rate for initial colonoscopy procedures attributed to incomplete colon cleansing and increasing the subject's willingness to undergo follow-up procedures.

In a first aspect, the invention is a composition for colonic cleansing that may include a phosphate salt and a flavorant that comprises aspartame and a citrate.

In a second aspect, the invention is a kit for colonic cleansing that may include monobasic sodium phosphate, dibasic sodium phosphate, aspartame, and a citrate.

In a third aspect, the invention is a method of colonic cleansing that may include administering orally to a subject an aqueous preparation including monobasic sodium phosphate, dibasic sodium phosphate, aspartame, and a citrate.

The scope of the present invention is defined solely by the appended claims, and is not affected to any degree by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

Figure 1:
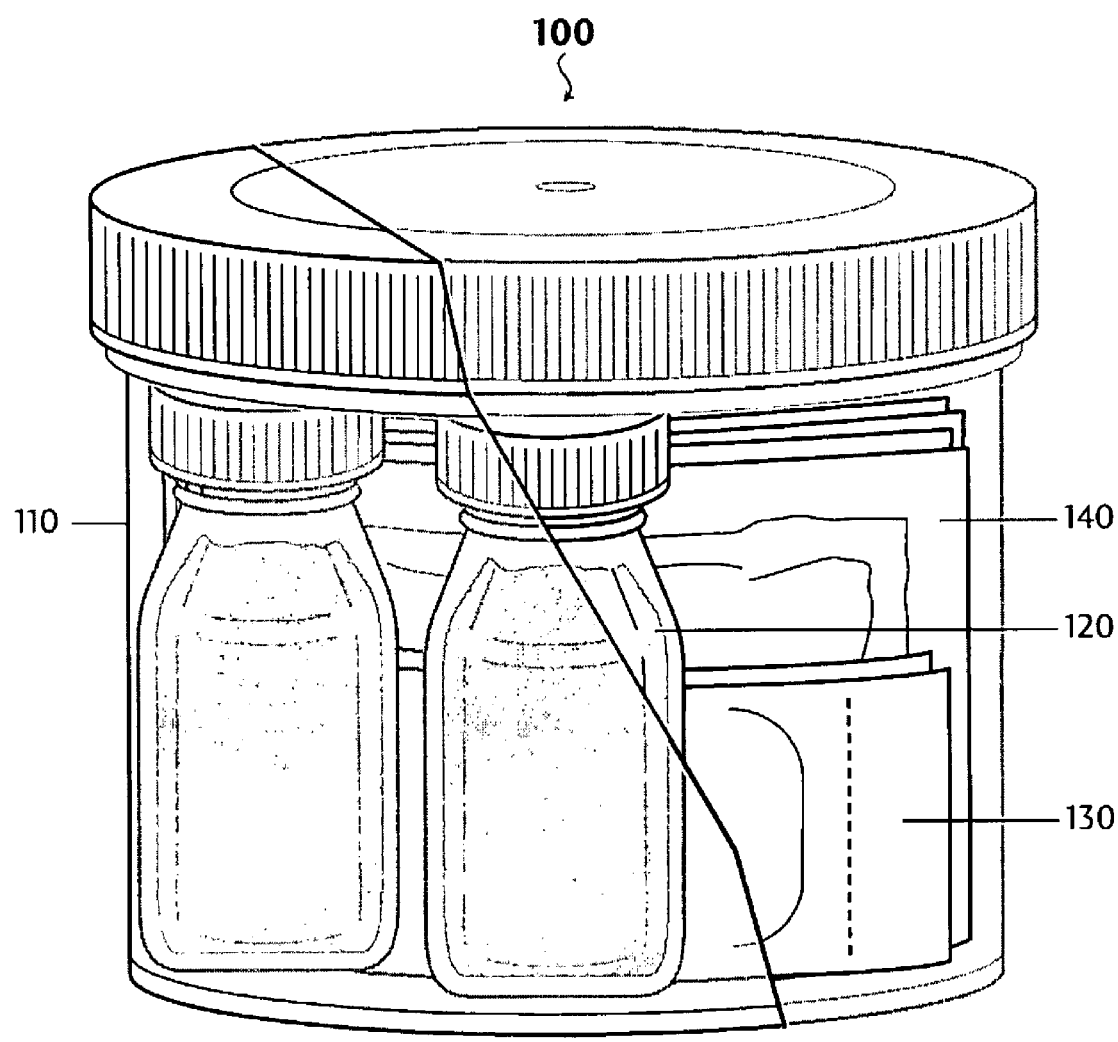
FIG. 1 depicts a cut-away view of a colonic cleansing kit having aspects of the present invention.

The present invention makes use of the discovery that adding a flavorant that includes aspartame and a citrate to a phosphate salt laxative significantly increases the palatability of the laxative. The resultant flavorant/phosphate salt formulations may improve subject compliance for both primary screening of asymptomatic colorectal carcinoma, and for return surveillance in those subjects who may benefit from more frequent colonoscopy. The discovery that flavorants that include aspartame and a citrate are substantially preferred in comparison to other flavoring regimes was unexpected.

Phosphate salt laxatives, such as commercially available FLEET® PHOSPHO-SODA® (C. B. Fleet, Lynchburg, Va.; National Formulary Monograph USP 23/NF18, p. 1430), include monobasic sodium phosphate (sodium dihydrogen phosphate, monohydrate) ($NaH_2PO_4 \cdot H_2O$) and dibasic sodium phosphate (disodium hydrogen phosphate, heptahydrate) ($Na_2HPO_4 \cdot 7H_2O$) in water. In one aspect, the phosphate salt laxative includes from 0.05 to 1.5 gram/mL of monobasic sodium phosphate and from 0.02 to 0.6 gram/mL of dibasic sodium phosphate. Phosphate salt laxatives have a pH from about 4.4 to about 5.2 and may be produced in multiple ways, such as by combining phosphoric acid with dibasic sodium phosphate or with caustic soda. Laxatives of this type are very stable, thus having a long shelf-life, and are considered to work in a mild and very effective manner.

In another aspect, the phosphate salt laxative includes from 0.25 to 1 or from 0.4 to 1 gram/mL of monobasic sodium phosphate and from 0.1 to 0.4 or from 0.13 to 0.25 gram/mL of dibasic sodium phosphate. At present, an especially preferred phosphate salt laxative includes about 0.48 g/mL of monobasic sodium phosphate and about 0.18 g/mL of dibasic sodium phosphate. Phosphate salt laxatives that include one phosphate salt, such as dibasic sodium phosphate, also may be used.

In addition to a water solution, the phosphate salt laxative may be incorporated into a gel. For example, an aqueous solution containing the phosphate salts may be combined with a gelling agent to form a gel. Suitable gelling agents may include gelatin, such as Gelatin, Type A, 25 Bloom, 50 mesh, from Great Lakes Gelatin, PO Box 917, Grayslake, Ill.; agar, such as Sigma brand Agar A-7002 Lot 71K0093; commercially available products that includes flavorings, such a JELL-O® brand dessert mix, and the like. In one aspect, about 85 grams of JELL-O® may be boiled in about 130 mL of water and combined with a near-boiling solution containing 45 mL of FLEET® PHOSPHO-SODA® diluted with about 65 mL of water and the flavorant. Additional details regarding the incorporation of a phosphate salt laxative into a gel may be found in US. Pat. App. 20040071779 A1.

Prior to consumption, the flavorant may be added to the phosphate salt laxative to increase its palatability. The flavorant includes aspartame and a citrate. The citrate may include citric acid, salts, such as sodium or potassium citrate, derivatives of citrate, such as a citrate derivatized with ester functionality, and the like. The flavorant also may include natural and/or artificial flavorings, such as natural and/or artificial fruit flavors, to further increase the palatability of the laxative.

The flavorant may be in the form of a commercially available aspartame-based drink mixture. One such product is CRYSTAL LIGHT® powder available from Kraft Foods, Northfield, Ill. CRYSTAL LIGHT® powder includes aspartame, citric acid, and fruit flavors that result in various drink flavors when the powder is combined with water. For example, lemonade flavored CRYSTAL LIGHT® powder includes citric acid, potassium citrate, aspartame, maltodextrin, magnesium oxide, natural flavor, acesulfame potassium, lemon juice solids, artificial color, yellow 5 lake, and BHA.

At present, CRYSTAL LIGHT® powder may be obtained that will make various drink flavors, including pink lemonade, lemonade, orange, tangerine-strawberry, raspberry-peach, and raspberry ice. Other drink favors, such as raspberry lemonade, raspberry, strawberry-kiwi, strawberry-orange-banana, pineapple-orange, and grapefruit also may be used as flavorants. At present, Pink Lemonade CRYSTAL LIGHT® powder is an especially preferred flavorant for combination with the phosphate salt laxative. Less preferred flavorants include natural sugars that may be digested, especially when the natural sugars are present in significant amounts. Digestion of such natural sugars may lead to hydrogen gas formation in the colon that can ignite during polypectomy.

Preferable compositions may include from 15 to 75 mL, from 30 to 60 mL, or from 40 to 50 mL of phosphate salt laxative in combination with from 1 to 10 grams, from 2 to 6 grams, or from 4 to 5 grams of CRYSTAL LIGHT® drink mix. The composition also may include from 240 to 480 mL, from 300 to 420 mL, or from 270 to 450 mL of water. At present, an especially preferred composition includes about 45 mL of a phosphate salt laxative that includes about 0.48 g/mL of monobasic sodium phosphate and about 0.18 g/mL of dibasic sodium phosphate, about 4.4 g of CRYSTAL LIGHT® Pink Lemonade powder, and about 360 mL of water.

In another aspect, the flavorant may be in the form of a reduced-filler aspartame-based mixture. In relation to a commercially available aspartame-based drink mixture, such as CRYSTAL LIGHT®, a reduced-filler aspartame-based mixture has a reduced amount of maltodextrin. Preferably, the reduced-filler mixture also contains less natural flavoring and flowability enhancers than commercially available drink mixtures. By reducing the amount of maltodextrin, natural flavoring, and the like, the amount of flavorant added to increase the palatability of the phosphate salt laxative may be reduced.

A preferable reduced-filler flavorant includes aspartame, citrates, artificial lemon flavoring, and plant extract. At present, an especially preferred plant extract for use in a reduced-filler flavorant is available from WILD Flavors, Inc., Erlanger, Ky. and is referred to as RESOLVER®. It is believed that the plant extracts in RESOLVER®occupy the receptors on the tongue that are responsible for bitter tastes, thus neutralizing the otherwise bitter aspects of the flavorant and/or the phosphate salt laxative.

In one aspect, from 1 to 3 grams, preferably about 2 grams of the reduced-filler aspartame-based mixture is added to 40 to 50 mL of the phosphate salt laxative. At present, an especially preferred composition includes about 45 mL of a phosphate salt laxative that includes about 0.48 g/mL of monobasic sodium phosphate and about 0.18 g/mL of dibasic sodium phosphate, 2.0 g+/−100% by weight of the reduced-filler aspartame-based mixture, and about 360 mL of water.

In one aspect, the phosphate salts and the flavorant are provided as dry powders that are mixed with water before administration to a subject. In another aspect, the phosphate salts are provided in water and mixed with the powdered flavorant. In another aspect, the phosphate salts and the flavorant are each provided in separate solutions, which are mixed before administration. If a gelling agent is used, the phosphate salts and the flavorant may be incorporated into the gel. In a preferred aspect, a kit is provided that includes a water-based composition including the phosphate salts that is mixed with the powdered flavorant before administration. In this aspect, the powdered flavorant also may include a powdered gelling agent. Additional water also may be added to the formulation.

The composition also may include ascorbic acid or a salt thereof. Due to the poor stability of ascorbic acid in solution, the ascorbic acid may be separately packaged and added to the phosphate salt laxative before use. In a preferred aspect, when the flavorant is packaged as a dry powder, the ascorbic acid may be packaged as a dry powder with the flavorant. When packaged as a dry powder, such as with the flavorant, the ascorbic acid may be coated to improve its stability. Suitable coatings include silicone, ethyl cellulose, and the like. In one aspect, enough ascorbic acid is added to provide a pre-administration solution concentration of from 0.25 to 50 g/L or from 1 to 25 g/L. Additional details regarding the use of ascorbic acid in laxative preparations may be found in U.S. Pat. No. 5,274,001.

FIG. 1 depicts a cut-away view of a colonic cleansing kit 100 having aspects of the present invention. The kit 100 includes an exterior package 110, one or more plastic containers 120, and one or more envelope containers 130 and 140. The exterior package 110 may have paper and/or plastic components. The exterior package 110 may enclose multiple containers, such as containers 120, 130, and 140, one or more supporting structures for the multiple containers, usually having paper and/or plastic components, instructions for use, and the like. The supporting structures may be formed from stiff paper, STYROFOAM™, and the like.

Figure 2A:
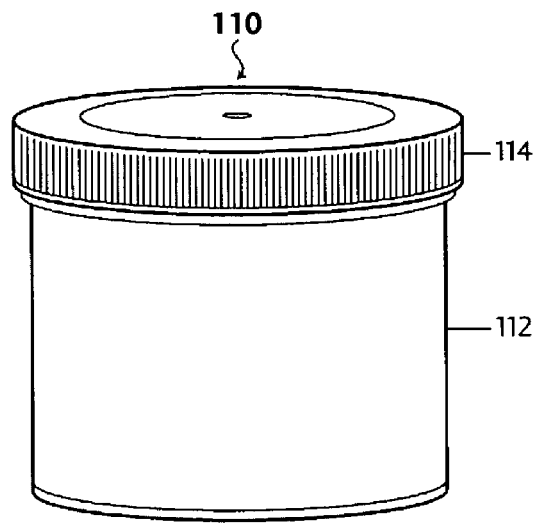
FIGS. 2A-2D depict individual components that may be found in a colonic cleansing kit having aspects of the present invention.

FIGS. 2A-2D depict the individual components that may be found in the colonic cleansing kit 100. As shown in FIG. 2A, the exterior package 110, may take the form of a plastic jar 112 having a removable screw-type lid 114. The diameter of the jar 112 may be about 8 cm. The diameter of the lid 112 may allow attachment to the jar 112.

Figure 2B:
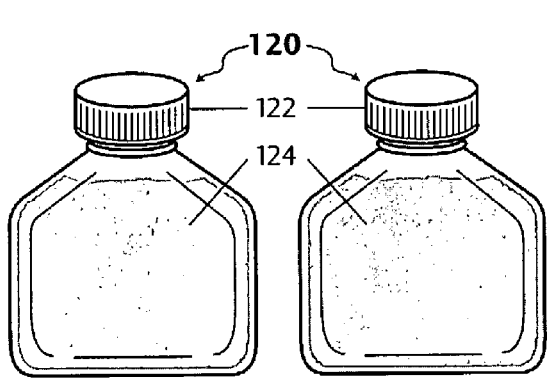
Figure 2C:
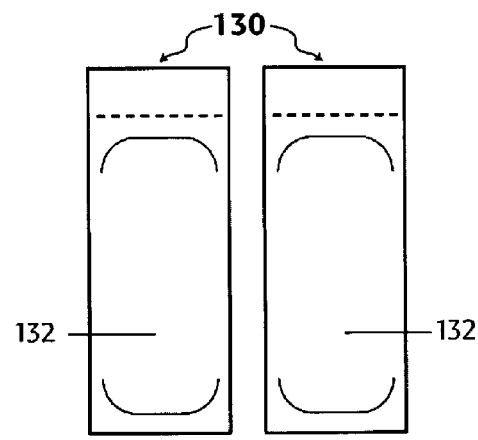
Figure 2D:
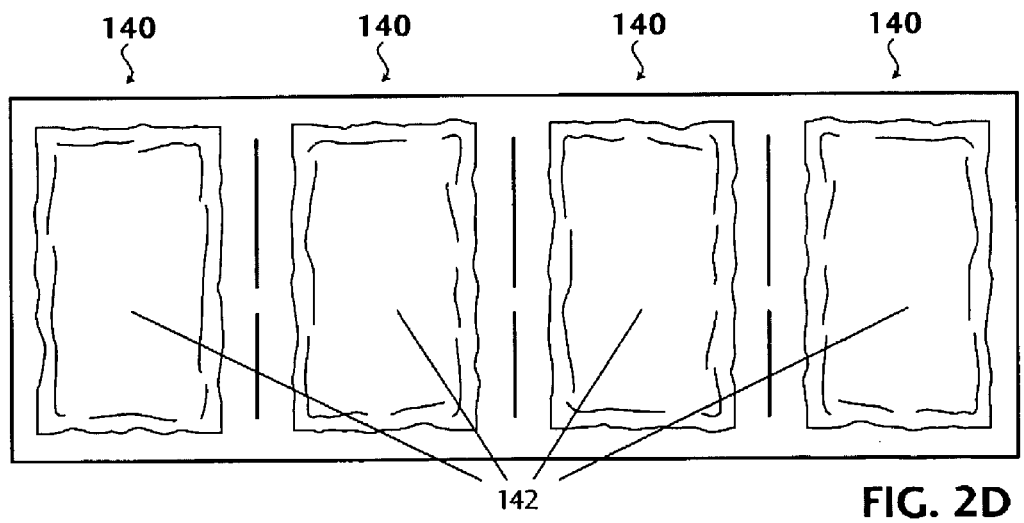

FIGS. 2B-2D depict various types of containers that may be included in the colonic cleansing kit 100. The containers may take the form of bottles, tubs, sachets, envelopes, tubes, ampoules, and the like, which may be formed in part or in whole from plastic, glass, paper, foil, MYLAR®, wax, and the like. The containers may be equipped with fully or partially detachable lids that may initially be part of the containers or may be affixed to the containers by mechanical, adhesive, or other means.

FIG. 2B depicts two plastic bottles 120 having screw-top lids 122, each containing about 45 mL of FLEET® PHOSPHO-SODA® liquid 124. FIG. 2C depicts two packets 130 made from foil-lined paper 132 that enclose the flavorant (not shown). The packets 130 may be rectangular in shape, having a width of about 4.1 to about 4.4 centimeters (cm) and a length of about 6.3 to about 7.6 cm. FIG. 2D depicts separate foil-lined paper envelopes 140 enclosing anorectal wipes 142. The anorectal wipes 142 may be in the form of pads and the like, such as FLEET® Pain-Relief Pre-Moistened anorectal pads. In one aspect, four individually wrapped wipes are preferred. The anorectal wipes 142 may be rectangular in shape, having dimensions of about 4 cm by about 7 cm.

The anorectal wipes 142 may be made from any suitable substrate, such as cloth, paper, or combinations thereof, and may be wetted with an aqueous solution that may include one or more active ingredients, such as a local anesthetic (Pramoxine Hydrochloride, for example) and a protectant (Glycerin, for example). The aqueous solution also may include one or more inactive ingredients, such as cetylpyridinium chloride, citric acid, disodium EDTA, eucalyptol, menthol, octoxynol-9, sodium benzoate, and sodium citrate.

The exterior package 110 of the kit 100 also may enclose an instruction sheet (not shown) that includes directions regarding when to consume the colonic cleansing composition in relation to the time of a colonoscopy procedure, how to combine the FLEET® PHOSPHO-SODA® liquid with the flavorant to form the colonic cleansing composition, and how to apply the relief wipes to provide the desired soothing effect.

By orally administering the compositions of the present invention to a subject, the colon may be cleansed. Generally, the compositions are administered so that from 0.4 to 0.85 grams of monobasic sodium phosphate and from 0.1 to 0.5 grams of dibasic sodium phosphate per kilogram of body weight are consumed. A first aliquot of the composition may be administered to the subject about 14 hours prior to the colonoscopy. This initial dose may be followed by a second aliquot of the composition administered about 3 hours prior to the colonoscopy. The subject should consume large amounts of liquids, 3 to 4 Liters for example, in addition to the composition to maintain adequate hydration. These additional liquids may include aqueous solutions that include oral re-hydration salts and/or electrolytes, such as GATORADE® and other oral re-hydration beverages.

In the examples below, it was unexpectedly discovered that subjects significantly preferred phosphate salt laxatives combined with the flavorant that included aspartame and citric acid in relation to other attempts to mask the taste of the laxative. The data below demonstrated that an aspartame and citrate containing flavorant proved superior at improving the palatability of a phosphate salt laxative. Furthermore, the aspartame containing flavorant significantly reduced the incidence of adverse events, including anal irritation and abdominal cramps, in relation to other flavoring regimes.

EXAMPLES

A study was undertaken to evaluate the preference, tolerance, and palatability of FLEET® PHOSPHO-SODA® laxative preparation flavored with flavoring regimes A through D in multiple subjects. Each 45 mL portion of FLEET® PHOSPHO-SODA® laxative included about 21.6 g of monobasic sodium phosphate (monohydrate) and about 8.1 g of dibasic sodium phosphate (heptahydrate). Flavoring regimes A through D are summarized as follows:

(A) FLEET® PHOSPHO-SODA® (45 mL) and ginger-lemon flavor in 720 mL of ginger ale (SCHWEPPES®). The resultant solution was split into three 8 oz. portions that were consumed 10 minutes apart.

(B) FLEET® PHOSPHO-SODA® (45 mL) and cola flavor in 360 mL of cold water. The resultant solution was consumed at once.

(C) FLEET® PHOSPHO-SODA® (45 mL) and ginger-lemon flavor in 120 mL of cold water. The resultant solution was consumed at once.

(D) FLEET® PHOSPHO-SODA® (45 mL) and CRYSTAL LIGHT® Pink Lemonade flavorant (~4.42 g) in 360 mL of cold water. The resultant solution was consumed at once.

Description of Study and Preparation Regimens.

The study employed a randomized, single-blind, balanced incomplete block (BIB) design for sequence (order of administration) and gender. Adult men and women who were scheduled to undergo colonoscopy were randomly given one of the flavoring regimes A through D at approximately 7:00 pm on the evening before the colonoscopy. A second, but different, flavoring regime A through D was given to the subject on the following morning, approximately 10-12 hours after the first dose and approximately 3 hours before the colonoscopy. For example, a single subject could receive flavoring regime A on the night before the procedure and flavoring regime B on the morning of the procedure to generate an "AB" preparation regimen.

Each of 72 subjects was randomly assigned to one of the twelve possible flavoring regimens (AB, BA, CB, BC, AD, DA, CD, DC, DB, BD, AC, and CA). This was accomplished by assigning each subject the next available flavoring regime depending on the subject's gender, based on the order in which they completed the screening evaluations; and then assigning the subject to the corresponding regimen from the randomization list. Two randomization lists were used, one for males and one for females, to assure balance of genders across the 12 treatment groups in the study.

The physician performing the colonoscopy procedure did not know which flavoring regimes had been given to each subject and the subjects were instructed not to discuss their preparation regimen with the physician. Each subject also was asked to consume additional clear fluids to assure adequate hydration.

The subjects completed a questionnaire to evaluate their acceptance, the tolerability, and the palatability of each flavoring regime after each of the two doses. After the morning flavoring regime was consumed, each subject also was asked questions regarding their preferences for the two flavor regimens they had experienced. These questions were directed preference questions, and also an open-ended question for the subjects to describe their experience.

Results and Evaluation.

Table 1 below illustrates the number of subjects that underwent each flavoring regimen (Total) and their overall preference rating (no preference between the morning and evening regimen, some preference for the morning or the evening regimen, or a large preference for the morning or the evening regimen), depending on when they were given the flavoring regimen. Generally, for pairs of flavoring regimens, preference ratings were similar regardless of which flavor was given first. All subjects who received the D regimen (FLEET® PHOSPHO-SODA® and CRYSTAL LIGHT® Pink Lemonade as a flavorant) expressed a preference for this regimen over all other regimens, regardless of their respective flavors.

TABLE 1

| Preparation Regimen | Morning Regimen | | | Evening Regimen | | Total Subjects | Preference Indication |
|---|---|---|---|---|---|---|---|
| | Large Preference | Some Preference | No Preference | Some Preference | Large Preference | | |
| AB | 3 | 1 | 1 | 1 | 0 | 6 | A ≈ B |
| BA | 0 | 3 | 0 | 2 | 1 | 6 | |
| CB | 0 | 1 | 1 | 1 | 3 | 6 | B > C |
| BC | 3 | 1 | 1 | 1 | 0 | 6 | |
| AD | 1 | 0 | 2 | 1 | 2 | 6 | D > A |
| DA | 4 | 0 | 0 | 1 | 1 | 6 | |
| CD | 0 | 1 | 0 | 4 | 2 | 7 | D >> C |
| DC | 5 | 0 | 0 | 0 | 1 | 6 | |
| DB | 4 | 0 | 2 | 0 | 0 | 6 | D > B |
| BD | 0 | 1 | 1 | 1 | 3 | 6 | |
| AC | 3 | 0 | 1 | 2 | 0 | 6 | A > C |
| CA | 1 | 1 | 1 | 1 | 2 | 6 | |
| Totals | 24 | 9 | 10 | 15 | 15 | 73 | |

Analysis of Items Relating to Adverse Events.

A linear model based on perceived intensity score was utilized to analyze each adverse event. Each event was scored twice by the subject, once in the evening and once in the morning, using the assigned flavoring regimen. The model had gender, flavor regimen, and time of administration as the factors. Models were tested for interactions, but the p-values were above the specified 0.10 level of significance; thus, the interaction terms were deleted and the models repeated with only the main effect terms.

The least squares means are presented below in Table 2 for each adverse event, in addition to the standard deviations and p-values by gender, flavoring regime, and time of administration. The table shows that adverse events were scored worse by females than by males. Furthermore, abdominal cramps, abdominal bloating, and indigestion were more intense during the evening administration than during the morning administration, while weakness/faint feeling, and thirst/dry mouth were worse during the morning.

The adverse event least square means for each of flavor regimes A through D are presented below in Table 3. The intensity of the adverse events were scored as 0=none, 1=mild, 2=moderate, and 3=severe. Surprisingly, flavor regimen was significantly related to anal irritation and abdominal cramping. Flavor regime D (FLEET® PHOSPHO-SODA® and CRYSTAL LIGHT® Pink Lemonade flavorant) showed from 34% to 53% less irritation than the other flavor regimes. Flavor regime D also showed from 60% to 54% less abdominal cramping than the other flavoring regimes. Furthermore, the intensity of abdominal bloating, weakness/faint feeling, and chills was also perceived to be lower by the subjects when using flavoring regimen D.

TABLE 3

| | Flavor Regimen | | | | |
|---|---|---|---|---|---|
| Adverse Event | A | B | C | D | Std Error |
| Nausea | 0.47 | 0.41 | 0.47 | 0.53 | 0.15 |
| Abdominal Bloating | 0.60 | 0.55 | 0.57 | 0.43 | 0.09 |
| Abdominal Cramps | 0.49 | 0.44 | 0.50 | 0.20 | 0.09 |
| Anal Irritation | 0.80 | 0.94 | 0.67 | 0.44 | 0.11 |

TABLE 2

| Adverse Event | Gender | | Time of Administration | | Std Err | Gender p-value | Flavor p-value | Time p-value |
|---|---|---|---|---|---|---|---|---|
| | Male | Female | PM | AM | | | | |
| Nausea | 0.26 | 0.67 | 0.42 | 0.52 | 0.05 | 0.0056 | 0.8215 | 0.2602 |
| Abdominal Bloating | 0.52 | 0.55 | 0.73 | 0.34 | 0.05 | 0.6594 | 0.5119 | <0.0001 |
| Abdominal Cramps | 0.30 | 0.52 | 0.57 | 0.25 | 0.05 | 0.0540 | 0.0545 | <0.0001 |
| Anal Irritation | 0.45 | 0.96 | 0.66 | 0.75 | 0.07 | 0.0052 | 0.0195 | 0.3555 |
| Weakness/Faint feeling | 0.13 | 0.24 | 0.06 | 0.30 | 0.04 | 0.1716 | 0.9195 | 0.0001 |
| Chills | 0.22 | 0.30 | 0.27 | 0.25 | 0.04 | 0.5257 | 0.2420 | 0.6876 |
| Headache | 0.15 | 0.37 | 0.20 | 0.32 | 0.05 | 0.0865 | 0.9520 | 0.1262 |
| Thirst/Dry Mouth | 0.24 | 0.33 | 0.18 | 0.38 | 0.05 | 0.3696 | 0.1591 | 0.0054 |
| Indigestion | 0.14 | 0.37 | 0.36 | 0.15 | 0.04 | 0.0173 | 0.5971 | 0.0014 |

TABLE 3-continued

| Adverse Event | Flavor Regimen | | | | Std Error |
|---|---|---|---|---|---|
| | A | B | C | D | |
| Weakness/Faint feeling | 0.21 | 0.18 | 0.21 | 0.14 | 0.07 |
| Chills | 0.22 | 0.30 | 0.36 | 0.16 | 0.07 |
| Headache | 0.24 | 0.30 | 0.24 | 0.26 | 0.08 |
| Thirst/Dry Mouth | 0.18 | 0.19 | 0.42 | 0.34 | 0.08 |
| Indigestion | 0.31 | 0.21 | 0.19 | 0.30 | 0.07 |

While various embodiments of the invention have been described, it will be apparent to those of ordinary skill in the art that other embodiments and implementations are possible within the scope of the invention. Accordingly, the invention is not to be restricted except in light of the attached claims and their equivalents

What is claimed is:

1. A composition for colonic cleansing comprising:
 a flavorant comprising aspartame, maltodextrin, acesulfame potassium, and a citrate; and
 a phosphate salt comprising from 0.4 to 1 gram/mL of monobasic sodium phosphate and from 0.13 to 0.25 gram/mL of dibasic sodium phosphate, where about 45 mL of the phosphate salt is combined with 2.0 g+/−10% by weight of the flavorant.

2. A kit for colonic cleansing, comprising the composition of claim 1.

3. A method for colonic cleaning, comprising:
 administering to a subject in need thereof the composition of claim 1, wherein the subject experiences less abdominal cramping and less anal irritation when compared to an otherwise identical composition except that the flavorant consists of cola flavor.

4. The composition of claim 1, where the composition further comprises a flavoring selected from the group consisting of natural fruit flavors, artificial fruit flavors, and combinations thereof.

5. The composition of claim 1, where the phosphate salt is present as a liquid comprising water and 0.48 gram/mL of monobasic sodium phosphate and 0.18 gram/mL of dibasic sodium phosphate.

6. The composition of claim 1, further comprising ascorbic acid or a salt thereof.

7. The kit of claim 2, where the flavorant further comprises a flavoring selected from the group consisting of natural fruit flavors, artificial fruit flavors, and combinations thereof.

8. The kit of claim 2, further comprising ascorbic acid or a salt thereof.

9. The kit of claim 2, further comprising at least one anorectal wipe, the anorectal wipe wetted with an aqueous solution including a local anesthetic and a skin protectant.

10. The method of claim 3, where the composition further comprises ascorbic acid or a salt thereof.

11. The method of claim 3, further comprising administering oral re-hydration liquids to the subject.

* * * * *

UNITED STATES PATENT AND TRADEMARK OFFICE
CERTIFICATE OF CORRECTION

| | | |
|---|---|---|
| PATENT NO. | : 7,867,521 B2 | Page 1 of 1 |
| APPLICATION NO. | : 11/574635 | |
| DATED | : January 11, 2011 | |
| INVENTOR(S) | : Nelson Ayala | |

It is certified that error appears in the above-identified patent and that said Letters Patent is hereby corrected as shown below:

Page 2

Col. 1, lines 8-9, delete "in vivo" and insert --*in vivo*--.
Col. 2, line 22, delete "INIKP" and insert --INKP--.

Page 4

Col. 2, line 13, delete "hrrp:"

Signed and Sealed this
Twenty-second Day of November, 2011

David J. Kappos
*Director of the United States Patent and Trademark Office*